United States Patent [19]
Liao et al.

[11] Patent Number: 5,877,013
[45] Date of Patent: Mar. 2, 1999

[54] RHODOSPORIDIUM D-AMINO ACID OXIDASE

[75] Inventors: Gwo-Jen Liao, Taipei; Yi-Jang Lee, Hsinchu; Yun-Huey Lee, Kaohsiung; Li-Lin Chen; Wen-Shen Chu, both of Hsinchu, all of Taiwan

[73] Assignee: Food Industry Research and Development Institute, Taiwan

[21] Appl. No.: 903,624

[22] Filed: Jul. 31, 1997

[51] Int. Cl.$^6$ .................................................. C12N 15/53
[52] U.S. Cl. .................................. 435/252.3; 435/320.1; 435/189; 536/23.2
[58] Field of Search ........................... 435/320.1, 252.3, 435/189; 536/23.2

[56] References Cited

U.S. PATENT DOCUMENTS

| | | | |
|---|---|---|---|
| 5,296,358 | 3/1994 | Battistel et al. | 435/49 |
| 5,597,704 | 1/1997 | Lee et al. | 435/25 |

FOREIGN PATENT DOCUMENTS

| | | |
|---|---|---|
| 0 364 275 A2 | 4/1990 | European Pat. Off. . |
| 0 496 993 A1 | 8/1992 | European Pat. Off. . |
| 96/27667 | 9/1996 | WIPO . |

OTHER PUBLICATIONS

ATCC Catalogue of Yeasts, 18th ed., 1990, pp. 51 & 52. AC–P80324 (1995).

Lee, C.C., et al. (1988) Science 239, 1288–1291.

Faotto et al., "Amino Acid Sequence of D–amino Acid Oxidase from the Yeast Rhnodotorula Gracilis", Flavins Flavoproteins, Proceed Int'l Symposium, 11th (1994), Meeting Date 1993 163–166, XP 000677151.

Fukui et al., "Molecular Cloning and Sequences Analysis of Conas Encoding Porcinc Kidney D–amino Acid Oxidase", Biochemistry 26:3612–3618, 1987.

Lee et al., "D–amino Acid Oxidase Activity from Rhodosporidium Toruloides", Abstracts of the Annual Meeting of the American Society for Microbiology 95:368, 1995, XP 002050710.

Berg et al., "Purification of D–amino Acid Oxidase from Trigonopsis Variabilis", Analytical Biochemistry, vol. 71, pp. 214–222 (1976).

Casalin et al., "A Study on Apoenzyme From *Rhodotorula gracilis* D–amino Acid Oxidase", Eur.J. Biochem., 197, 513–517 (1991).

Faotto et al., "The Primary Structure of D–amino Acid Oxidase From *Rhodotorula gracilis*", Biotechnology Letters, vol. 17 No. 2 (Feb 1995) pp. 193–198.

Groningen, "The Yeasts: a taxonomic study", Elsevier Science Publishers B.V., 1984, pp. 892–905, 508–531.

Isogai et al., "Structure and Expression of cDNA for D–amino Acid Oxidase Active Against Cephalosporin C From Fusarium Solani", J. Biochem. vol. 108, No. 6, 1990, pp. 1063–1069.

Kim et al., "Simple and Rapid Determination of the Activity of Recombinant D–amino Acid Oxidase in Cephalosporin C Bioconversion with Use of a Micro $pO_2$ Probe", Biotechnology Techniques, vol. 9 No. 12, 863–868.

Lee et al., "Bioconversion of Cephalosporin C with D–amino Acid Oxidase from the Yeast Rhodosporidium Toruloides", Biotechnology Letters, vol. 16 No.5 (May 1994) pp. 467–472.

Pilone et al., "A Process For Bioconversion of Cephalosporin C By *Rhodotorula gracilis* D–amino Acid Oxidase", Biotechnology Letters, vol. 17 No. 2 (Feb. 1995) pp. 199–204 (Dec. 1995) pp. 863–868.

Simonetta et al., "D–amino Acid Oxidase Activity in the Yeast *Rhodotorula gracilis*", Microbiology Letters, vol. 15 (1982) pp. 27–31.

Simonetta et al., "Properties of D–amino Acid Oxidase from *Rhodotorula gracilis*", Eur. J. Biochem 180, pp. 199–204 (1989).

Simonetta, et al., "Purification and Properties of D–amino Acid Oxidase, an Inducible Flavoenzyme From *Rhodotorula gracilis*", Biochimica et Biophysica Acta 914 (1987) pp. 136–142.

Simonetta et al., "Induction of D–amino Acid Oxidase by D–alanine in *Rhodotorula gracilis* Grown in Defined Medium", Journal of General Microbiology (1989), 135, 593–600.

Vicenzi et al., "Enzymatic Oxidation of Cephalosporin C Using Whole Cells of the Yeast Triginopsis Variabilis Within a 'cross–flow filter–reactor'", Enzyme Microb. Tech., 1993, vol. 15., Apr., pp. 281–285.

*Primary Examiner*—Charles L. Patterson, Jr.
*Attorney, Agent, or Firm*—Fish & Richardson P.C.

[57] ABSTRACT

This invention relates to a D-amino acid oxidase of the genus Rhodosporidium and a gene encoding it.

6 Claims, No Drawings

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
( A ) LENGTH: 1458 base pairs
( B ) TYPE: nucleic acid
( C ) STRANDEDNESS: double
( D ) TOPOLOGY: linear ( i i ) MOLECULE TYPE: Genomic DNA ( x i ) SEQUENCE DESCRIPTION: SEQ ID NO:1:

| | | | | | |
|---|---|---|---|---|---|
| ATGCACTCTC | AGAAGCGCGT | CGTTGTCCTC | GGATCAGGCG | GTGCGTCTTT | TCCCTCTCCT | 60 |
| CCCCACACCC | GACAGTCCTC | GACGAGGTGT | AGGACGGCGA | GCAAAGCTGC | CGAGGGCGAT | 120 |
| CTGGGCTGAC | TGAGCGCTCG | AGTGTACAGT | TATCGGTCTG | AGCAGCGCCC | TCATCCTCGC | 180 |
| TCGGAAGGGC | TACAGCGTGC | ATATTCTCGC | GCGCGACTTG | CCGGAGGACG | TCTCGAGCCA | 240 |
| GACTTTCGCT | TCACCATGGG | CTGTGCGTCG | TCTCACTGTA | GTTGGAGGAT | GTCAGCGAGA | 300 |
| GCTGATCAAT | CTCGTCATCC | CCGCAGGGCG | CGAATTGGAC | GCCTTTCATG | ACGCTTACAG | 360 |
| ACGGTCCTCG | ACAAGCAAAA | TGGGAAGAAT | CGACTTTGTC | GTCTCCTTC  | TACCTCATTC | 420 |
| TTGGCCTCGA | GCTGACGAGT | GTATGATACA | CAGCAAGAAG | TGGGTCGAGT | TGGTCCCGAC | 480 |
| GGGCCATGCC | ATGTGGCTCA | AGGGACGAG  | GCGGTTCGCG | CAGAACGAAG | ACGGCTTGCT | 540 |
| CGGGCACTGG | TACAAGGACA | TCACGCCAAA | TGTGCGCCCA | CATTCACTCT | TCCCTTCGCA | 600 |
| TGTCTCCGTT | TACTGACCCG | CCCTCTTTCG | CCGTGCGCAG | TACCGCCCCC | TCCCATCTTC | 660 |
| CGAATGTCCA | CCTGGCGCTA | TCGGCGTAAC | CTACGACACC | CTCTCCGTCC | ACGCACCAAA | 720 |
| GTACTGCCAG | TACCTTGCAA | GAGAGCTGCA | GAAGCTCGGC | GCGACGTTTG | AGAGACGGAC | 780 |
| CGTTACGTCG | CTTGAGCAGG | CGTTCGACGG | TGCGGATTTG | GTGGTCAACG | CTACGGGACT | 840 |
| TGGTATGTCC | CGAACTGCCC | CTCTCTACCT | GCAATTTTGC | TGATTGATAT | GCTCGCAGGC | 900 |
| GCCAAGTCGA | TTGCGGGCAT | CGACGACCAA | GCCGCCGAGC | CAATCCGCGG | CCAAACCGTC | 960 |
| CTCGTCAAGT | CCCCATGCAA | GCGATGCACG | ATGGACTCGT | CCGACCCCGC | TTCTCCCGCC | 1020 |
| TACATCATTC | CCCGACCAGG | TGGCGAAGTC | ATCTGCGGCG | GGACGTACGG | CGTGGGAGAC | 1080 |
| TGGGACTTGT | CTGTCAACCC | AGAGACGGTC | CAGCGGATCC | TCAAGCACTG | CTTGCGCCTC | 1140 |

-continued

```
GACCCGACCA  TCTCGAGCGA  CGGAACGATC  GAAGGCATCG  AGGTCCTCCG  CCACAACGTC    1200

GGCTTGCGAC  CTGCACGACG  AGGCGGACCC  CGCGTCGAGG  CAGAACGGAT  CGTCCTGCCT    1260

CTCGACCGGA  CAAAGTCGCC  CCTCTCGCTC  GGCAGGGGCA  GCGCACGAGC  CGCGAAGGAG    1320

AAGGAGGTCA  CGCTTGTGCA  TGCGTATGGC  TTCTCGAGTG  CGGGATACCA  GCAGAGTTGG    1380

GGCGCGGCGG  AGGATGTCGC  GCAGCTCGTC  GACGAGGCGT  TCCAGCGGTA  CCACGGCGCG    1440

GCGCGGGAGT  CGAAGTTG                                                     1458
```

( 2 ) INFORMATION FOR SEQ ID NO:2:

( i ) SEQUENCE CHARACTERISTICS:
        ( A ) LENGTH: 1104 base pairs
        ( B ) TYPE: nucleic acid
        ( C ) STRANDEDNESS: single
        ( D ) TOPOLOGY: linear ( i i ) MOLECULE TYPE: cDNA ( i x ) FEATURE:
        ( A ) NAME/KEY: Coding Sequence
        ( B ) LOCATION: 1...1104

( x i ) SEQUENCE DESCRIPTION: SEQ ID NO:2:

```
ATG  CAC  TCT  CAG  AAG  CGC  GTC  GTT  GTC  CTC  GGA  TCA  GGC  GTT  ATC  GGT       48
Met  His  Ser  Gln  Lys  Arg  Val  Val  Val  Leu  Gly  Ser  Gly  Val  Ile  Gly
 1                  5                   10                  15

CTG  AGC  AGC  GCC  CTC  ATC  CTC  GCT  CGG  AAG  GGC  TAC  AGC  GTG  CAT  ATT       96
Leu  Ser  Ser  Ala  Leu  Ile  Leu  Ala  Arg  Lys  Gly  Tyr  Ser  Val  His  Ile
              20                  25                  30

CTC  GCG  CGC  GAC  TTG  CCG  GAG  GAC  GTC  TCG  AGC  CAG  ACT  TTC  GCT  TCA      144
Leu  Ala  Arg  Asp  Leu  Pro  Glu  Asp  Val  Ser  Ser  Gln  Thr  Phe  Ala  Ser
         35                  40                  45

CCA  TGG  GCT  GGC  GCG  AAT  TGG  ACG  CCT  TTC  ATG  ACG  CTT  ACA  GAC  GGT      192
Pro  Trp  Ala  Gly  Ala  Asn  Trp  Thr  Pro  Phe  Met  Thr  Leu  Thr  Asp  Gly
     50                  55                  60

CCT  CGA  CAA  GCA  AAA  TGG  GAA  GAA  TCG  ACT  TTC  AAG  AAG  TGG  GTC  GAG      240
Pro  Arg  Gln  Ala  Lys  Trp  Glu  Glu  Ser  Thr  Phe  Lys  Lys  Trp  Val  Glu
 65                  70                  75                      80

TTG  GTC  CCG  ACG  GGC  CAT  GCC  ATG  TGG  CTC  AAG  GGG  ACG  AGG  CGG  TTC      288
Leu  Val  Pro  Thr  Gly  His  Ala  Met  Trp  Leu  Lys  Gly  Thr  Arg  Arg  Phe
                      85                  90                  95

GCG  CAG  AAC  GAA  GAC  GGC  TTG  CTC  GGG  CAC  TGG  TAC  AAG  GAC  ATC  ACG      336
Ala  Gln  Asn  Glu  Asp  Gly  Leu  Leu  Gly  His  Trp  Tyr  Lys  Asp  Ile  Thr
                 100                 105                 110

CCA  AAT  TAC  CGC  CCC  CTC  CCA  TCT  TCC  GAA  TGT  CCA  CCT  GGC  GCT  ATC      384
Pro  Asn  Tyr  Arg  Pro  Leu  Pro  Ser  Ser  Glu  Cys  Pro  Pro  Gly  Ala  Ile
             115                 120                 125

GGC  GTA  ACC  TAC  GAC  ACC  CTC  TCC  GTC  CAC  GCA  CCA  AAG  TAC  TGC  CAG      432
Gly  Val  Thr  Tyr  Asp  Thr  Leu  Ser  Val  His  Ala  Pro  Lys  Tyr  Cys  Gln
         130                 135                 140

TAC  CTT  GCA  AGA  GAG  CTG  CAG  AAG  CTC  GGC  GCG  ACG  TTT  GAG  AGA  CGG      480
Tyr  Leu  Ala  Arg  Glu  Leu  Gln  Lys  Leu  Gly  Ala  Thr  Phe  Glu  Arg  Arg
145                 150                 155                 160

ACC  GTT  ACG  TCG  CTT  GAG  CAG  GCG  TTC  GAC  GGT  GCG  GAT  TTG  GTG  GTC      528
Thr  Val  Thr  Ser  Leu  Glu  Gln  Ala  Phe  Asp  Gly  Ala  Asp  Leu  Val  Val
                 165                 170                 175

AAC  GCT  ACG  GGA  CTT  GGC  GCC  AAG  TCG  ATT  GCG  GGC  ATC  GAC  GAC  CAA      576
Asn  Ala  Thr  Gly  Leu  Gly  Ala  Lys  Ser  Ile  Ala  Gly  Ile  Asp  Asp  Gln
             180                 185                 190

GCC  GCC  GAG  CCA  ATC  CGC  GGC  CAA  ACC  GTC  CTC  GTC  AAG  TCC  CCA  TGC      624
Ala  Ala  Glu  Pro  Ile  Arg  Gly  Gln  Thr  Val  Leu  Val  Lys  Ser  Pro  Cys
         195                 200                 205
```

| | | | | | | | | | | | | | | | | |
|---|---|---|---|---|---|---|---|---|---|---|---|---|---|---|---|---|
| AAG | CGA | TGC | ACG | ATG | GAC | TCG | TCC | GAC | CCC | GCT | TCT | CCC | GCC | TAC | ATC | 672 |
| Lys | Arg | Cys | Thr | Met | Asp | Ser | Ser | Asp | Pro | Ala | Ser | Pro | Ala | Tyr | Ile | |
| 210 | | | | | 215 | | | | | 220 | | | | | | |
| ATT | CCC | CGA | CCA | GGT | GGC | GAA | GTC | ATC | TGC | GGC | GGG | ACG | TAC | GGC | GTG | 720 |
| Ile | Pro | Arg | Pro | Gly | Gly | Glu | Val | Ile | Cys | Gly | Gly | Thr | Tyr | Gly | Val | |
| 225 | | | | | 230 | | | | | 235 | | | | | 240 | |
| GGA | GAC | TGG | GAC | TTG | TCT | GTC | AAC | CCA | GAG | ACG | GTC | CAG | CGG | ATC | CTC | 768 |
| Gly | Asp | Trp | Asp | Leu | Ser | Val | Asn | Pro | Glu | Thr | Val | Gln | Arg | Ile | Leu | |
| | | | | 245 | | | | | 250 | | | | | 255 | | |
| AAG | CAC | TGC | TTG | CGC | CTC | GAC | CCG | ACC | ATC | TCG | AGC | GAC | GGA | ACG | ATC | 816 |
| Lys | His | Cys | Leu | Arg | Leu | Asp | Pro | Thr | Ile | Ser | Ser | Asp | Gly | Thr | Ile | |
| | | | 260 | | | | | 265 | | | | | 270 | | | |
| GAA | GGC | ATC | GAG | GTC | CTC | CGC | CAC | AAC | GTC | GGC | TTG | CGA | CCT | GCA | CGA | 864 |
| Glu | Gly | Ile | Glu | Val | Leu | Arg | His | Asn | Val | Gly | Leu | Arg | Pro | Ala | Arg | |
| | | 275 | | | | | 280 | | | | | 285 | | | | |
| CGA | GGC | GGA | CCC | CGC | GTC | GAG | GCA | GAA | CGG | ATC | GTC | CTG | CCT | CTC | GAC | 912 |
| Arg | Gly | Gly | Pro | Arg | Val | Glu | Ala | Glu | Arg | Ile | Val | Leu | Pro | Leu | Asp | |
| 290 | | | | | 295 | | | | | 300 | | | | | | |
| CGG | ACA | AAG | TCG | CCC | CTC | TCG | CTC | GGC | AGG | GGC | AGC | GCA | CGA | GCC | GCG | 960 |
| Arg | Thr | Lys | Ser | Pro | Leu | Ser | Leu | Gly | Arg | Gly | Ser | Ala | Arg | Ala | Ala | |
| 305 | | | | | 310 | | | | | 315 | | | | | 320 | |
| AAG | GAG | AAG | GAG | GTC | ACG | CTT | GTG | CAT | GCG | TAT | GGC | TTC | TCG | AGT | GCG | 1008 |
| Lys | Glu | Lys | Glu | Val | Thr | Leu | Val | His | Ala | Tyr | Gly | Phe | Ser | Ser | Ala | |
| | | | | 325 | | | | | 330 | | | | | 335 | | |
| GGA | TAC | CAG | CAG | AGT | TGG | GGC | GCG | GCG | GAG | GAT | GTC | GCG | CAG | CTC | GTC | 1056 |
| Gly | Tyr | Gln | Gln | Ser | Trp | Gly | Ala | Ala | Glu | Asp | Val | Ala | Gln | Leu | Val | |
| | | | 340 | | | | | 345 | | | | | 350 | | | |
| GAC | GAG | GCG | TTC | CAG | CGG | TAC | CAC | GGC | GCG | GCG | CGG | GAG | TCG | AAG | TTG | 1104 |
| Asp | Glu | Ala | Phe | Gln | Arg | Tyr | His | Gly | Ala | Ala | Arg | Glu | Ser | Lys | Leu | |
| | | 355 | | | | | 360 | | | | | 365 | | | | |

( 2 ) INFORMATION FOR SEQ ID NO:3:

( i ) SEQUENCE CHARACTERISTICS:
        ( A ) LENGTH: 368 amino acids
        ( B ) TYPE: amino acid
        ( D ) TOPOLOGY: linear ( i i ) MOLECULE TYPE: protein ( v ) FRAGMENT TYPE: internal ( x i ) SEQUENCE DESCRIPTION: SEQ ID NO:3:

| | | | | | | | | | | | | | | | |
|---|---|---|---|---|---|---|---|---|---|---|---|---|---|---|---|
| Met | His | Ser | Gln | Lys | Arg | Val | Val | Val | Leu | Gly | Ser | Gly | Val | Ile | Gly |
| 1 | | | | 5 | | | | | 10 | | | | | 15 | |
| Leu | Ser | Ser | Ala | Leu | Ile | Leu | Ala | Arg | Lys | Gly | Tyr | Ser | Val | His | Ile |
| | | | 20 | | | | | 25 | | | | | 30 | | |
| Leu | Ala | Arg | Asp | Leu | Pro | Glu | Asp | Val | Ser | Ser | Gln | Thr | Phe | Ala | Ser |
| | | 35 | | | | | 40 | | | | | 45 | | | |
| Pro | Trp | Ala | Gly | Ala | Asn | Trp | Thr | Pro | Phe | Met | Thr | Leu | Thr | Asp | Gly |
| | 50 | | | | | 55 | | | | | 60 | | | | |
| Pro | Arg | Gln | Ala | Lys | Trp | Glu | Glu | Ser | Thr | Phe | Lys | Lys | Trp | Val | Glu |
| 65 | | | | | 70 | | | | | 75 | | | | | 80 |
| Leu | Val | Pro | Thr | Gly | His | Ala | Met | Trp | Leu | Lys | Gly | Thr | Arg | Arg | Phe |
| | | | | 85 | | | | | 90 | | | | | 95 | |
| Ala | Gln | Asn | Glu | Asp | Gly | Leu | Leu | Gly | His | Trp | Tyr | Lys | Asp | Ile | Thr |
| | | | 100 | | | | | 105 | | | | | 110 | | |
| Pro | Asn | Tyr | Arg | Pro | Leu | Pro | Ser | Ser | Glu | Cys | Pro | Pro | Gly | Ala | Ile |
| | | 115 | | | | | 120 | | | | | 125 | | | |
| Gly | Val | Thr | Tyr | Asp | Thr | Leu | Ser | Val | His | Ala | Pro | Lys | Tyr | Cys | Gln |

|     |     |     |     | 130 |     |     |     |     | 135 |     |     |     |     | 140 |     |
|-----|-----|-----|-----|-----|-----|-----|-----|-----|-----|-----|-----|-----|-----|-----|-----|

Tyr Leu Ala Arg Glu Leu Gln Lys Leu Gly Ala Thr Phe Glu Arg Arg
145                     150                     155                     160

Thr Val Thr Ser Leu Glu Gln Ala Phe Asp Gly Ala Asp Leu Val Val
                165                     170                     175

Asn Ala Thr Gly Leu Gly Ala Lys Ser Ile Ala Gly Ile Asp Asp Gln
            180                     185                     190

Ala Ala Glu Pro Ile Arg Gly Gln Thr Val Leu Val Lys Ser Pro Cys
        195                     200                     205

Lys Arg Cys Thr Met Asp Ser Ser Asp Pro Ala Ser Pro Ala Tyr Ile
    210                     215                     220

Ile Pro Arg Pro Gly Gly Glu Val Ile Cys Gly Gly Thr Tyr Gly Val
225                     230                     235                     240

Gly Asp Trp Asp Leu Ser Val Asn Pro Glu Thr Val Gln Arg Ile Leu
                245                     250                     255

Lys His Cys Leu Arg Leu Asp Pro Thr Ile Ser Ser Asp Gly Thr Ile
            260                     265                     270

Glu Gly Ile Glu Val Leu Arg His Asn Val Gly Leu Arg Pro Ala Arg
        275                     280                     285

Arg Gly Gly Pro Arg Val Glu Ala Glu Arg Ile Val Leu Pro Leu Asp
    290                     295                     300

Arg Thr Lys Ser Pro Leu Ser Leu Gly Arg Gly Ser Ala Arg Ala Ala
305                     310                     315                     320

Lys Glu Lys Glu Val Thr Leu Val His Ala Tyr Gly Phe Ser Ser Ala
                325                     330                     335

Gly Tyr Gln Gln Ser Trp Gly Ala Ala Glu Asp Val Ala Gln Leu Val
            340                     345                     350

Asp Glu Ala Phe Gln Arg Tyr His Gly Ala Ala Arg Glu Ser Lys Leu
        355                     360                     365

( 2 ) INFORMATION FOR SEQ ID NO:4:

( i ) SEQUENCE CHARACTERISTICS:
        ( A ) LENGTH: 190 base pairs
        ( B ) TYPE: nucleic acid
        ( C ) STRANDEDNESS: double
        ( D ) TOPOLOGY: linear ( i i ) MOLECULE TYPE: Genomic DNA ( x i ) SEQUENCE DESCRIPTION: SEQ ID NO:4:

AAGCTTCGGC ACGAGCATGA GTGTGAATGA TGGTCCAAGG AGGACAGCGC AGAGTCAACA    60

GGAGGGCACA TGGAGGCAGA GCGTGGGGCG GAGGAGGCAG ATGGGAGTC GCGCTGGGGG    120

ACGAGGGGGT GTCGCTCGAC TAACAGCTCT CTATCGCTCT TGCTGCTGCT TGTACTACTC    180

GAACGACGCC    190

( 2 ) INFORMATION FOR SEQ ID NO:5:

( i ) SEQUENCE CHARACTERISTICS:
        ( A ) LENGTH: 801 base pairs
        ( B ) TYPE: nucleic acid
        ( C ) STRANDEDNESS: single
        ( D ) TOPOLOGY: linear ( i i ) MOLECULE TYPE: Genomic DNA ( x i ) SEQUENCE DESCRIPTION: SEQ ID NO:5:

GGCGGGATTT GTGGCTGTAT TGCGGGCATC TACAAGACCA GCTTCATCTC GGACGACAAC    60

| | | | | | |
|---|---|---|---|---|---|
| ACGAGAGCGG | CGAGTCTTCG | TACCGTCTGA | CCTTCGCAAT | CCGCCGAGTC | CTTGCCCGTT | 120 |
| GCCCTGCTTG | CTCCTTTCGT | ATCTCCTGTG | ACTCGGAACG | TCGCTCTTCG | CCTCTGTCAC | 180 |
| TTGCCAGGCC | GTCCCTTCAA | ACTGTCGCCG | CCCTCCTCCT | CCCAATCTCC | TCCTCACGCG | 240 |
| ACTTGCCACT | ACTCTCACTT | CTCCTGCTTA | CCAAGGCTTA | CACTACGCAA | CACTAAGCGC | 300 |
| GGCATCAGGT | TCCGTTGCGC | GCCTCGTCAC | GACCCGACTT | TTTTTCGCCC | GTTCGCTCGC | 360 |
| CTCGCTCCGT | TGCCGAGCGA | AGAACTTCGC | CTGCCTTCGA | ATCTCTCGCC | TTGCTCGTCT | 420 |
| CGTCCTGCTC | CGTTCCACCA | CAGATAGACT | CACAGCAACA | CACTCACAAT | GGTCAAGGTG | 480 |
| CGCACCCACT | CCCGCCAGTC | CAACTCGCGC | GACGAGAGAC | CACCGTCTCG | TTGACATCAC | 540 |
| TGACCTCGTC | GCTCGCCACC | CACCCTCCCG | CTCGTCCATG | CACACAGGCA | GCACCACGAT | 600 |
| CAGACGAGCA | GCAGCACTAC | CACGCCACAG | TCATGGGCGG | ACTCAAGGGC | GGCGCGATGG | 660 |
| GGTTGGCGGC | GGGTGGAGCG | GGTGCGGTTG | CGCTGCAGAG | GGCGAACGTA | CAGGCGTTCA | 720 |
| CGAGGTTGAC | GCTGCCTCTC | AAGGCGTTTG | CTGTCACGTA | CGTCCCGCGA | TCCCTTACTA | 780 |
| TGCGACTCCC | TCGGTGAATT | C | | | | 801 |

( 2 ) INFORMATION FOR SEQ ID NO:6:

( i ) SEQUENCE CHARACTERISTICS:
        ( A ) LENGTH: 16 base pairs
        ( B ) TYPE: nucleic acid
        ( C ) STRANDEDNESS: single
        ( D ) TOPOLOGY: linear ( i i ) MOLECULE TYPE: degenerate oligonucleotide ( x i ) SEQUENCE DESCRIPTION: SEQ ID NO:6:

AARTA Y TG Y C AR-TA Y C       16

( 2 ) INFORMATION FOR SEQ ID NO:7:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: degenerate oligonucleotide ( x i ) SEQUENCE DESCRIPTION: SEQ ID NO:7:

ATNGA Y GA Y C A Y GC-NGC       17

( 2 ) INFORMATION FOR SEQ ID NO:8:

( i ) SEQUENCE CHARACTERISTICS:
        ( A ) LENGTH: 17 base pairs
        ( B ) TYPE: nucleic acid
        ( C ) STRANDEDNESS: single
        ( D ) TOPOLOGY: linear ( i i ) MOLECULE TYPE: degenerate oligonucleotide ( x i ) SEQUENCE DESCRIPTION: SEQ ID NO:8:

GCNGC Y TGRT CRTCNAT       17

( 2 ) INFORMATION FOR SEQ ID NO:9:

( i ) SEQUENCE CHARACTERISTICS:
        ( A ) LENGTH: 17 base pairs
        ( B ) TYPE: nucleic acid
        ( C ) STRANDEDNESS: single ( D ) TOPOLOGY: linear ( i i ) MOLECULE TYPE: degenerate oligonucleotide ( x i ) SEQUENCE DESCRIPTION: SEQ ID NO:9:

ATGGA YAGY-AGYGAYCC 17

( 2 ) INFORMATION FOR SEQ ID NO:10:

( i ) SEQUENCE CHARACTERISTICS:
( A ) LENGTH: 22 amino acids
( B ) TYPE: amino acid
( D ) TOPOLOGY: linear ( i i ) MOLECULE TYPE: peptide ( x i ) SEQUENCE DESCRIPTION: SEQ ID NO:10:

Met His Ser Gln Lys Arg Val Val Val Leu Gly Ser Gly Val Ile Gly
1               5                   10                  15
Leu Ser Ser Ala Leu Ile
            20

( 2 ) INFORMATION FOR SEQ ID NO:11:

( i ) SEQUENCE CHARACTERISTICS:
( A ) LENGTH: 10 amino acids
( B ) TYPE: amino acid
( D ) TOPOLOGY: linear ( i i ) MOLECULE TYPE: peptide ( x i ) SEQUENCE DESCRIPTION: SEQ ID NO:11:

Tyr Cys Gln Tyr Leu Ala Arg Glu Leu Gln
1               5                   10

( 2 ) INFORMATION FOR SEQ ID NO:12:

( i ) SEQUENCE CHARACTERISTICS:
( A ) LENGTH: 14 amino acids
( B ) TYPE: amino acid
( D ) TOPOLOGY: linear ( i i ) MOLECULE TYPE: peptide ( x i ) SEQUENCE DESCRIPTION: SEQ ID NO:12:

Ile Ala Gly Gly Ile Asp Asp Gln Ala Ala Glu Pro Ile Arg
1               5                   10

( 2 ) INFORMATION FOR SEQ ID NO:13:

( i ) SEQUENCE CHARACTERISTICS:
( A ) LENGTH: 9 amino acids
( B ) TYPE: amino acid
( D ) TOPOLOGY: linear ( i i ) MOLECULE TYPE: peptide ( x i ) SEQUENCE DESCRIPTION: SEQ ID NO:13:

Arg Cys Thr Met Asp Ser Ser Asp Pro
1               5

( 2 ) INFORMATION FOR SEQ ID NO:14:

( i ) SEQUENCE CHARACTERISTICS:
( A ) LENGTH: 8 amino acids
( B ) TYPE: amino acid
( D ) TOPOLOGY: linear (i i) MOLECULE TYPE: peptide (x i) SEQUENCE DESCRIPTION: SEQ ID NO:14:

Ile Ala Gly Ile Asp Asp Gln Ala
1               5

(2) INFORMATION FOR SEQ ID NO:15:

(i) SEQUENCE CHARACTERISTICS:
        (A) LENGTH: 214 base pairs
        (B) TYPE: nucleic acid
        (C) STRANDEDNESS: double
        (D) TOPOLOGY: linear (i i) MOLECULE TYPE: genomic DNA (x i) SEQUENCE DESCRIPTION: SEQ ID NO:15:

```
AAGTACTGCC AGTACCTTGC AAGAGAGCTG CAGAAGCTCG GCGCGACGTT TGAGAGACGG      60
ACCGTTACGT CGCTTGAGCA GGCGTTCGAC GGTGCGGATT TGGTGGTCAA CGCTACGGGA     120
CTTGGTATGT CCCGAACTGC CCCTCTCTAC CTGCAATTTT GCTGATTGAT ATGCTCGCAG     180
GCGCCAAGTC GATTGCGGGC ATCGACGACC AAGC                                 214
```

(2) INFORMATION FOR SEQ ID NO:16:

(i) SEQUENCE CHARACTERISTICS:
        (A) LENGTH: 10 base pairs
        (B) TYPE: nucleic acid
        (C) STRANDEDNESS: double
        (D) TOPOLOGY: linear (i i) MOLECULE TYPE: Kozak sequence (x i) SEQUENCE DESCRIPTION: SEQ ID NO:16:

CCACCATGGC          10

(2) INFORMATION FOR SEQ ID NO:17:

(i) SEQUENCE CHARACTERISTICS:
        (A) LENGTH: 8 base pairs
        (B) TYPE: nucleic acid
        (C) STRANDEDNESS: double
        (D) TOPOLOGY: linear (i i) MOLECULE TYPE: consensus (x i) SEQUENCE DESCRIPTION: SEQ ID NO:17:

Y GTGT-
T Y Y          8

(2) INFORMATION FOR SEQ ID NO:18:

(i) SEQUENCE CHARACTERISTICS:
        (A) LENGTH: 8 base pairs
        (B) TYPE: nucleic acid
        (C) STRANDEDNESS: double
        (D) TOPOLOGY: linear (i i) MOLECULE TYPE: genomic DNA (x i) SEQUENCE DESCRIPTION: SEQ ID NO:18:

TGTATTGC          8

RHODOSPORIDIUM D-AMINO ACID OXIDASE

BACKGROUND OF THE INVENTION

D-amino acid oxidase ("DAO") is a flavoprotein known to be able to convert cephalosporin C ("Ceph C") to α-ketoadipyl cephalosporanic acid ("α-ketoadipyl 7-ACA), hydrogen peroxide, and ammonia. α-ketoadipyl 7-ACA, upon reaction with hydrogen peroxide, can be further transformed into glutaryl-7-aminocephalosporanic acid ("GL-7-ACA"). Since GL-7-ACA is a starting material for the production of cephem antibiotics, DAO is of great industrial interest.

Besides the production of α-keto acids (Tosa et al., Agric Biol Chem [1974] 38, 1529–1536), DAO has been used in the resolution of racemic mixtures of amino acids (Tu et al., Separation Sci [1972] 7, 403–408) and analytical determination of amino acids (Guilbault et al., Anal Chim Acta [1971] 56, 285–290). DAO can be found in various microorganisms, insects and animals.

SUMMARY OF THE INVENTION

This invention relates to an isolated nucleic acid encoding a DAO of the genus Rhodosporidium, e.g., *R. diobovatum, R. sphaerocarpum, R. kratochvilovae, R. toruloides, R. lusitaniae, R. paludignenum, R. dacryoidum, R. babjevae,* and *R. fluviale.* The term "D-amino acid oxidase of the genus Rhodosporidium" refers to any natural or man-made variant of DAO of the genus Rhodosporidium. For example, the nucleic acid can have the sequence SEQ ID NO: 1 or SEQ ID NO: 2 (both shown below), have a sequence which hybridizes under stringent conditions to SEQ ID NO: 1 or 2, or have a sequence which encodes the protein of SEQ ID NO: 3.

A vector and transformed host cell containing such a nucleic acid is included within the scope of this invention. By "vector" is meant any nucleic acid molecule or virus containing regulatory elements or reporter genes for the purpose of, but not limited to, expression in prokaryotic or eukaryotic cells or organisms. By "transformed host cell" is meant a host cell into which (or into an ancestor of which) has been introduced, by means of molecular biological techniques, a nucleic acid encoding a DAO from the genus Rhodosporidium. After introduction into the cell, this nucleic acid can exist extrachromosomally or become integrated into the host genome.

The present invention also relates to an isolated DAO of the genus Rhodosporidium, such as SEQ ID NO: 3 (shown below) or a protein which differs from SEQ ID NO: 3 by at least one conservative amino acid substitution.

The term "nucleic acid" encompasses both RNA and DNA, including cDNA, genomic DNA, and synthetic (e.g., chemically synthesized or modified) DNA. The nucleic acid may be double-stranded or single-stranded. Where single stranded, the nucleic acid may be a sense strand or an antisense strand. The term "isolated nucleic acid" refers to a nucleic acid which may be flanked by non-natural sequences, such as those of a plasmid or virus. Thus, the nucleic acid can include none, some, or all of the 5' non-coding (e.g., promoter) sequences which are immediately contiguous to the coding sequence. The term, therefore, includes, for example, a recombinant DNA which is incorporated into a vector including an autonomously replicating plasmid or virus, or into the genomic DNA of a prokaryote or eukaryote other than Rhodosporidium, or which exists as a separate molecule (e.g., a cDNA or a genomic DNA fragment produced by PCR or restriction endonuclease treatment) independent of other sequences. The term also includes a recombinant DNA or RNA which is part of a hybrid gene encoding an additional polypeptide sequence. Moreover, the term is meant to include nucleic acid fragments which are not naturally occurring as fragments and would not be found in the natural state.

By "hybridizes under stringent conditions" is meant the conditions in which a nucleic acid forms a stable, sequence-specific, non-covalent bond with the nucleic acid of SEQ ID NO: 1 or SEQ ID NO: 2 in solution or on solid support under the low salt and high temperature conditions regarded as stringent and set forth in Sambrook et al (Molecular Cloning, A Laboratory Manual, Sambrook, J., Fritsch, E. F., and Maniatis, T., 2nd ed. [1989] Cold Spring Harbor Laboratory Press). For example, reference nucleic acids such as SEQ ID NO: 1 or SEQ ID NO: 2 can be immobilized on nitrocellulose filters, and any other nucleic acids specifically and non-covalently binding to the immobilized reference nucleic acids in the presence of 0.2× SSC (1.75 g/l NaCl, 0.88 g/l $Na_3$citrate.$2H_2O$; pH 7.0) and 0.1% (w/v) sodium dodecylsulfate at 68° C. are considered to be hybridized under stringent conditions.

An "isolated D-amino acid oxidase" refers to a DAO which is purified or enriched from its natural environment (e.g., a DAO-rich extract prepared from host cells transformed with a DAO expression vector). A "conservative substitution" refers to a substitution, for example, within one of the following groups: valine, isoleucine, and leucine; aspartic acid and glutamic acid; asparagine and glutamine; serine and threonine; lysine and arginine; and phenylalanine and tyrosine.

The isolation and characterization of the Rhodosporidium DAO gene will allow the production of variant forms of the DAO proteins which may have advantageous activities such as a decreased $K_m$ for substrate conversion or greater protein stability.

Other features or advantages of the present invention will be apparent from the following drawings and detailed description of several embodiments, and also from the appending claims.

DETAILED DESCRIPTION OF THE INVENTION

This invention relates to DAO of the genus Rhodosporidium, e.g., *R. diobovatum, R. sphaerocarpum, R. kratochvilovae, R. toruloides, R. lusitaniae, R. paludignenum, R. dacryoidum, R. babjevae,* and *R. fluviale,* and a nucleic acid encoding a Rhodosporidium DAO.

Contemplated within the scope of this invention are recombinant nucleic acids or viruses which allow production of DAO protein in a transformed cell or transgenic organism or ease of specific or non-specific mutations within the DAO reading frame. These recombinant nucleic acids or viruses may further include any one of a variety of sequences upstream of the DAO coding sequences, such as strong constitutive promoters; within the DAO coding sequence, such as introns containing cis-elements that allow high level expression; or downstream of the DAO coding sequence, such as efficient polyadenylation signals. The invention further includes any cells containing or producing such nucleic acids or viruses, and any DAO proteins produced from such cells.

Without further elaboration, it is believed that one skilled in the art can, based on the above disclosure and the isolation of a DAO protein and a DAO gene from *R. toruloides* described below, utilize the present invention to its fullest extent. The following two examples are to be construed as merely illustrative of how one skilled in the art can isolate DAO genes and proteins from any species of the genus Rhodosporidium, and are not limitative of the remainder of the disclosure in any way whatsoever. Any publications cited in this disclosure are hereby incorporated by reference.

EXAMPLE 1

This example illustrates the purification and characterization of a D-amino acid oxidase active against cephalosporin C from Rhodosporidium.

R. toruloides, obtained from the American Type Culture Collection (No. 10788), was used as a source for the isolation of DAO protein.

The protein was purified as follows: (1) D-alanine was added to cell free extract of R. toruloides to final concentration of 0.3M, and mixture heated to 70° C. for 4 min. (2) The precipitate was removed by centrifugation at 13,000× g for 40 min. (3) The supernatant was dialyzed against 1.5 l of buffer A (50 mM potassium phosphate buffer, pH 8.0, 2 mM EDTA, 5 mM β-mercaptoethanol, 1 mM PMSF, and 2.5 g/ml pepstatin A). (4) The dialyzed protein solution was applied to a DEAE-Sephacel column (15×2.4 cm) and eluted with buffer A. Fractions with DAO activities were collected and concentrated in an Amicon cell (YM 30). (5) The concentrate was applied to a phenyl-Sepharose CL-4B column (15×2.0 cm) that had been equilibrated with 150 ml of buffer B (same as buffer A, but without pepstatin A) supplemented with 20% glycerol. The bound DAO was eluted with buffer B supplemented with 40% glycerol. Fractions with DAO activities were collected and dialyzed against 1.5 l of buffer B containing 10% glycerol. (6) The dialysate was concentrated to 2 ml and chromatographed on a fast protein liquid chromatography (FPLC) Mono Q HR 5/5 column previously equilibrated with 30 ml of buffer B supplemented with 10% glycerol. DAO was eluted immediately after the void volume. Fractions containing enzyme activities were pooled and concentrated to 1 ml. (7) The concentrate was applied to an FPLC gel-filtration Superose 12 HR 10/30 column and eluted with buffer B containing 10% glycerol and 0.25M NaCl. The active fractions were pooled and stored at −20° C.

The final chromatography used Superose 12 HR column, which allows gel permeation and effectively eliminated minor impurities from the protein sample.

Purified DAO, 0.88 mg, was obtained from about 100 g (wet weight) of R. toruloides cells with a yield of 21% and a specific activity of 60 U/mg of protein. (DAO unit activity definitions and assay conditions were given in Lee et al., Biotechnol Lett [1994] 16, 467–472.) The preparation yielded a single band in native PAGE. The enzyme was not susceptible to staining with periodic acid/Schiff's reagent, indicating that it was not a glycoprotein.

The molecular weight of the native enzyme was estimated to be 72 kDa by gel-filtration on an FPLC Superose 12 column as compared with a standard curve of reference proteins. SDS/PAGE revealed a single band with a molecular mass of 37 kDa. The results suggest that the native form of R. toruloides DAO consisted of two subunits of identical size. The $NH_2$-terminal amino acid sequence of the first 22 residues was determined to be Met His Ser Gln Lys Arg Val Val Val Leu Gly Ser Gly Val Ile Gly Leu Ser Ser Ala Leu Ile (SEQ ID NO: 10).

The absorption spectrum of DAO from R. toruloides showed two maxima, one each at 370 nm and 455 nm, which were typical for flavin chromophores. The E280/E455 ratio, a parameter frequently used to estimate the purity of a flavoprotein, was 8.1. High performance liquid chromatography (HPLC) analyses showed the flavin released from a boiled protein preparation had the same retention time as that of standard flavin adenine dinucleotide (FAD). The concentration of FAD was determined to be 6.34 g/ml, which was extracted from an protein solution of 0.297 mg/ml. Based on this result and SDS/PAGE analysis, a ratio of about 1.73 moles FAD/mole protein was obtained, indicating there was one FAD in each subunit.

The enzyme activity of DAO was measured at various temperatures. The protein exhibited maximal activity at 35° C. The enzyme was active (above 70% of maximal activity) at a temperature range of 30°–50° C. The enzyme activity decreased sharply at 60° C. to 30% of maximal activity. The enzyme was unstable at temperatures above 35° C. Only 20% and 10% of maximal activity were retained after incubation for 10 min. at 40° C. and 45° C., respectively.

The optimal pH for DAO activity was 9.0. The enzyme was active over a pH range of 7.5–10.0. DAO was stable at a pH range of 7.0–8.0 where more than 80% residual activity was detected. However, considerable activity was lost at pH above 8.5 with 70% inactivation at pH 11.0.

The relative activities of the purified DAO on various D-amino acid substrates were measured. The purified enzyme was active on all D-amino acids tested. The best substrate was D-tryptophan, followed by D-methionine, D-phenylalanine, D-alanine, and D-leucine. The enzyme exhibited less activity (<20% of maximal) for D-threonine, D-glutamic acid, D-aspartic acid, and D-lysine. No activity on L-amino acids, including L-alanine, L-proline, L-phenylalanine, and L-methionine, was detected. The apparent $K_m$ for each one of D-tryptophan, D-methionine, D-alanine and D-serine was 0.18 mM, 0.22 mM, 0.68 mM, and 3.4 mM, respectively. The enzyme was inhibited by 72%, 49%, and 21% in the presence of p-aminobenzoic acid, benzoic acid, and nicotinic acid, respectively. These aromatic acids were all determined to be competitive inhibitors for R. toruloides DAO. p-Aminobenzoic acid had the lowest $K_i$ (0.3 mM) among the aromatic acids tested.

The purified DAO protein, having the sequence SEQ ID NO: 3 (shown below), was used to convert Ceph C. The enzyme was 95% active on Ceph C as compared with its activity against D-alanine. The apparent $K_m$ of the enzyme for Ceph C is 0.65 mM. The yield was 91%, and further incubation did not increase the yield. No exogenous $H_2O_2$ was required for the reaction.

EXAMPLE 2

This example illustrates the isolation and expression of the D-amino acid oxidase gene from Rhodosporidium.

The DAO protein from R. toruloides was purified as described in example 1 above. The last two column chromatographies, Mono Q HR 5/5 and Supersoe 10 HR, were substituted by sodium dodecylsulfate (SDS)/polyacrylamide gel electrophoresis (PAGE). Approximately 300 picomoles of DAO was purified from an SDS/PAGE gel and peptide sequences were determined by the Protein and Nucleic Acid Facility, Stanford University, USA. Three internal peptide sequences (YCQYLARELQ [SEQ ID NO: 11], IAGGIDDQAAEPIR [SEQ ID NO: 12], and RCTMDSSDP [SEQ ID NO: 13]) were determined. To isolate the DAO gene from R. toruloides, four fully degenerate oligonucleotide primers were synthesized on the basis of the peptide sequences. They were primer 1

5'-AARTAYTGYCARTAYC-3'(SEQ ID NO: 6), primer 2
5'-ATNGAYGAYCAYGCNGC-3'(SEQ ID NO: 7), primer 3
5'-GCNGCYTGRTCRTCNAT-3'(SEQ ID NO: 8), and
primer 4 5'-ATGGAYAGYAGYGAYCC-3'(SEQ ID NO: 9),
where N represents G, A, T or C; Y represents T or C; and
R represents A or G.

PCR reactions with chromosomal DNA of R. toruloides as a template generated no product when primer 1 was used alone. There were several non-specific products synthesized in PCR reactions containing only primer 2, 3, or 4. PCR reactions with primers 2 and 4 also gave several non-specific products. A typical result using primer 1 and 3 was a specific PCR product about 210 bp in length, in addition to non-specific products. When this fragment was used as template, it could be reamplified by primers 1 and 3 in a PCR reaction.

The nucleotide sequence of the fragment was determined. It consisted of the 214 nucleotides shown below:
5'-AAGTACTGCCAGTACCTTGCAAGAGAGCTGCAG-AAGCTCGGCGCGACGTTTGAGAGA CGGACCGT-TACGTCGCTTGAGCAGGCGTTCGACGGT-GCGGATTTGGTGGTCAACGCTACG GGACTTGgtat-gtcccgaactgcccctctctacctgcaattttgctgattgatatgctcg cagGCGCCAAGTCGATTGCGGGCATCGACGACCAAGC-3'
(SEQ ID NO: 15)
(Lower case letters represent intron sequences, based on the cDNA described below.)
YCQYLARELQ (SEQ ID NO: 11) and IAGIDDQA (SEQ ID NO: 14), portions of the deduced amino acid sequence encoded by the 214 bp fragment, are identical to a part of the determined DAO protein sequence. The result indicated that the 214 bp DNA fragment is a portion of the gene encoding R. toruloides DAO. The fragment was then used as a probe for isolating the DAO gene.

Southern blot hybridization with the digoxigenin-labeled 214 bp DNA fragment described above identified a hybridizing fragment of about 3.3 kb. A mini-genomic DNA library was constructed by inserting HindIII-digested genomic DNA fragments with sizes ranging from 3.0 to 3.5 kb into pBluescript SK+. The library was screened with the same probe. Fifteen positive clones with two levels of intensity in signal on autoradiograms were obtained from screening approximately 200 bacterial colonies. Three random clones from each type were selected and analyzed for restriction enzyme profiles of the inserts. The results showed that these clones contained two different DNA inserts, resulting in the two levels of intensity in signal. One type of clones was chosen for further study based on their higher intensity in signal and the hybridization profile of the insert with the 214 bp probe. These clones were found to contain a genomic DNA fragment which contained the DAO gene sequence. The genomic sequence of the DAO gene coding region is shown below:
5'-ATGCACTCTCAGAAGCGCGTCGTTGTCCTCGG-ATCAGGCGgtgcgtcttttccct ctcctccccacacccgacagtcctcgac-gaggtgtaggacggcgagcaaagctgccgagg gcgatctgggctgact-gagcgctcgagtgtacagTTATCGGTCT-GAGCAGCGCCCTCATCCTCGCTCGGAAGGGCTACAGCGTG-CATATTCTCGCGCGCGACTTGCCGGAG-GACGTCTCG AGCCAGACTTTCGCTTCAC-CATGGGCTgtgcgtcgtctcactgtagttggaggatgtcag cgagagctgatcaatctcgtcatccccg-cagGGCGCGAATTGGACGCCTTTCATGACGCT TACAGACGGTCCTCGACAAGCAAAATGG-GAAGAATCGACTTTgtgcgtctccttctacct cattcttggcctc-gagctgacgagtgtatgatacacagCAA-GAAGTGGGTCGAGTTGGTC
CCGACGGGCCATGCCATGTGGCT-CAAGGGGACGAGGCGGTTCGCGCAGAAC-GAAGACGGC TTGCTCGGGCACTGGTACAAGGA-CATCACGCCAAATgtgcgcccacattcactcttccct tcgcatgtctccgtttactgacccgc-cctctttcgccgtgcgcagTACCGCCCCCTCCCA TCTTC-CGAATGTCCACCTGGCGCTATCGGCG-TAACCTACGACACCCTCTCCGTCCACGCA CCAAAGTACTGCCAGTACCTTGCAA-GAGAGCTGCAGAAGCTCGGCGC-GACGTTTGAGAGA CGGACCGTTACGTCGCTT-GAGCAGGCGTTCGACGGTGCGGATTTGGTGGT-CAACGCTACG GGACTTGgtatgtcccgaactgc-ccctctctacctgcaattttgctgattgatatgctcg cagGCGCCAAGTC-GATTGCGGGCATCGACGACCAAGCCGC-CGAGCCAATCCGCGGCCAAA CCGTCCTCGTCAAGTCCCCATGCAAGC-GATGCACGATGGACTCGTCCGACCCCGCTTCTC CCGCCTACATCATTCCCCGACCAGGTG-GCGAAGTCATCTGCGGCGGGACGTACGGCGTGG GAGACTGGGACTTGTCTGTCAACCCA-GAGACGGTCCAGCGGATCCTCAAGCACTGCTTGC GCCTCGACCCGACCATCTCGAGCGACG-GAACGATCGAAGGCATCGAGGTCCTCCGCCACA ACGTCGGCTTGCGACCTGCACGACGAG-GCGGACCCCGCGTCGAGGCAGAACGGATCGTCC TGCCTCTCGACCGGACAAAGTCGC-CCCTCTCGCTCGGCAGGGGCAGCGCAC-GAGCCGCGA AGGAGAAGGAGGTCACG-CTTGTGCATGCGTATGGCTTCTCGAGT-GCGGGATACCAGCAGA GTTGGGGCGCGGCGGAG-GATGTCGCGCAGCTCGTCGACGAGGCGT-TCCAGCGGTACCACG GCGCGGCGCGGGAGTCGAAGTTG-3' (SEQ ID NO: 1)
(The lower case letters represent intron sequences, based on the cDNA described below.)

5' and 3' rapid amplification of cDNA ends (RACE) were performed to isolate the cDNA ends for the DAO gene. RACE was performed using RACE kit from Gibco BRL according to manufacturer's protocols. DNA fragments of about 550 bp and 720 bp were amplified in 5'RACE and 3'RACE, respectively. These fragments were cloned into a pGEM-T vector for the determination of nucleotide sequences. The results showed that the two cDNA fragments have a 124-bp overlapping region. The combination of the nucleotide sequences of the two fragments generated an open reading frame (ORF) predicted to encode an amino acid sequence which contains regions with perfect identity to the three internal peptides described above. The coding region of the cDNA of DAO is shown below as.
5'-ATGCACTCTCAGAAGCGCGTCGTTGTCCTCGG-ATCAGGCGTTATCGGTCTGAGCAGC GCCCTCATC-CTCGCTCGGAAGGGCTACAGCGTG-CATATTCTCGCGCGCGACTTGCCGGAG GACGTCTCGAGCCAGACTTTCGCTTCACCATGGG-CTGGCGCG-AATTGGACGCCTTTCATG ACGCTTACAGACGGTC-CTCGACAAGCAAAATGGGAAGAATC-GACTTTCAAGAAGTGGGTC GAGTTGGTC-CCCGACGGGCCATGCCATGTGGCTCAAGGGGACG-AGGCGGTTCGCGCAGAAC GAAGACGGCT-TGCTCGGGCACTGGTACAAGGACAT-CACGCCAAATTACCGCCCCCTCCCA TCTTCCGAATGTCCACCTGGCGCTATCGGCGTAA-CCTACGACACC-CTCTCCGTCCACGCA CCAAAGTACTGCCAGTACCT-TGCAAGAGAGCTGCAGAAGCTCGGCGC- GACGTTTGAGAGA CGGACCGTTACGTCGCTTGAG-
CAGGCGTTCGACG
GTGCGGATTTGGTGGTCA-
ACGCTACG GGACTTGGCGCCAAGTCGAT-
TGCGGGCATCGACGACCAAGCCGC-
CGAGCCAATCCGCGGC CAAACCGTCCTC-
GTCAAGTCCCCATGCAAGCGATGCACGATGGACTC-
GTCCGACCCCGCTTCTCCCGCCTACAT-
CATTCCCCGACCAGGTGGCGAAGT-
CATCTGCGGCGGGACGTACGGC
GTGGGAGACTGGGACTTGTCTGTCAACCCA-
GAGACGGTCCAGCGG-ATCCTCAAGCACTGC
TTGCGCCTCGACCCGACCATCTCGAGC-
GACGGAACGATCGAAGGCATCGAGGTCCTCCGC
CACAACGTCGGCTTGCGACCTGCACGAC-
GAGGCGGACCCCGCGTCGAGGCAGAACGGATC
GTCCTGCCTCTCGACCGGACAAAGTCGC-
CCCTCTCGCTCGGCAGGGGCAGCGCACGAGCC
GCGAAGGAGAAGGAGGTCACGCTTGTG-
CATGCGTATGGCTTCTCGAGTGCGGGATACCAG
CAGAGTTGGGGCGCGGCGGAGGAT-
GTCGCGCAGCTCGTCGACGAGGCGTTC-
C A G C G G T A C
CACGGCGCGGCGCGGGAGTCGAAGTTG-3' (SEQ ID
NO: 2)

The ORF is 1104 nucleotides long, and encodes a protein of 368 amino acids with a molecular weight of 40,079 Da. The sequence of the protein, from the N-terminus to the C-terminus, is shown below:

```
M  H  S  Q  K  R  V  V  V  L  G  S  G  V  I  G  L  S  S  A
L  I  L  A  R  K  G  Y  S  V  H  I  L  A  R  D  L  P  E  D
V  S  S  Q  T  F  A  S  P  W  A  G  A  N  W  T  P  F  M  T
L  T  D  G  P  R  Q  A  K  W  E  E  S  T  F  K  K  W  V  E
L  V  P  T  G  H  A  M  W  L  K  G  T  R  R  F  A  Q  N  E
D  G  L  L  G  H  W  Y  K  D  I  T  P  N  Y  R  P  L  P  S
S  E  C  P  P  G  A  I  G  V  T  Y  D  T  L  S  V  H  A  P
K  Y  C  Q  Y  L  A  R  E  L  Q  K  L  G  A  T  F  E  R  R
T  V  T  S  L  E  Q  A  F  D  G  A  D  L  V  V  N  A  T  G
L  G  A  K  S  I  A  G  I  D  D  Q  A  A  E  P  I  R  G  Q
T  V  L  V  K  S  P  C  K  R  C  T  M  D  S  S  D  P  A  S
P  A  Y  I  I  P  R  P  G  G  E  V  I  C  G  G  T  Y  G  V
G  D  W  D  L  S  V  N  P  E  T  V  Q  R  I  L  K  H  C  L
R  L  D  P  T  I  S  S  D  G  T  I  E  G  I  E  V  L  R  H
N  V  G  L  R  P  A  R  R  G  G  P  R  V  E  A  E  R  I  V
L  P  L  D  R  T  K  S  P  L  S  L  G  R  G  S  A  R  A  A
K  E  K  E  V  T  L  V  H  A  Y  G  F  S  S  A  G  Y  Q  Q
S  W  G  A  A  E  D  V  A  Q  L  V  D  E  A  F  Q  R  Y  H
G  A  A  R  E  S  K  L    (SEQ ID NO:3)
```

Comparison of the nucleotide sequences between the cDNA and the genomic DNA revealed that the DAO gene contains six exons and five introns (see SEQ ID NO: 1 above). The sizes of the introns of the DAO gene were relatively small, ranging from 56 bp to 109 bp. Both ends of all five introns contained the exon-intron junction consensus sequence GT ...... AG.

The nucleotide sequence immediately 5' to the start codon and around the putative translation start site of the DAO gene is in accordance with the consensus sequence CCACC ATGGC (SEQ ID NO: 16) (Kozak, Nuc Acids Res [1984] 12, 857–872), in which the nucleotide in position –3 (where the A residue of the start codon is designated +1) is always a G or an A. The sequence 5' to the start codon is given below:
5'-AAGCTTCGGCACGAGCATGAGTGTGAATGATG-
GTCCAAGGAGGACAGCGCAGAGTCA ACAG-
GAGGGCACATGGAGGCA-
GAGCGTGGGGCGGAGGAGGCAGATGGG-
GAGTCGCGCTGG
GGGACGAGGGGGTGTCGCTCGACTAA-
CAGCTCTCTATCGCTCTTGCTGCTGCTTGTACTA
CTCGAACGACGCC-3' (SEQ ID NO: 4)

Consistent with fungal genes, no apparent TATA box is found in the 5' flanking region of the R. toruloides DAO gene.

In the sequence immediately 3' to the ORF, there is no consensus sequence for the polyadenylation signal. However, the sequence TGTATTGC (SEQ ID NO: 18) located 11 to 18 residues upstream from the poly(A) addition site resembled the sequence YGTGTTYY (SEQ ID NO: 17) (where Y represents pyrimidines) known to be involved in the formation of a correct 3' termini in mammalian mRNA. The sequence 3' to the ORF is shown below:
5'-GGCGGGATTTGTGGCTGTATTGCGGGCATCTA
CAAGACCAGCTTCATCTCGGACGAC AACAC-
GAGAGCGGCGAGTCTTCGTACCGTCT-
GACCTTCGCAATCCGCCGAGTCCTTGCCC
GTTGCCCTGCTTGCTCCTTTCGTATCTCCTGTG-
ACTCGGAACGTCGCTCTTCGCCTCTGT CACTTGC-
CAGGCCGTCCCTTCAAACTGTCGCCGC-
CCTCCTCCTCCCAATCTCCTCCTCAC
GCGACTTGCCACTACTCTCACTTCTCCTGCTTAC-
CAAGGCTTACACTACGCAACACTAAG CGCGGCAT-
CAGGTTCCGTTGCGCGCCTCGTCACGAC-
CCGACTTTTTTTCGCCCGTTCGCT
CGCCTCGCTCCGTTGCCGAGCGAAGAACTTCGCC-
TGCCTTCGAATCTCTCGCCTTGCTCG TCTCGTCCT-
GCTCCGTTCCACCACAGATAGACTCA-
CAGCAACACACTCACAATGGTCAAG GTGC-
GCACCCACTCCCGCCAGTC-
CAACTCGCGCGACGAGAGACCAC-
CGTCTCGTTGACAT CACTGACCTCGTCG-
CTCGCCACCCACCCTCCCGCTCGTCCAT-
GCACACAGGCAGCACCAC GATCAGACGAGCAG-
CAGCACTACCACGCCACAGTCATGGGCG-
GACTCAAGGGCGGCGCGA
TGGGGTTGGCGGCGGGTGGAGCGGGT-
GCGGTTGCGCTGCAGAGGGCGAACGTACAGGCGT
TCACGAGGTTGACGCTGCCTCTCAAG-
GCGTTTGCTGTCACGTACGTCCCGCGATCCCTTA
CTATGCGACTCCCTCGGTGAATTC-3' (SEQ ID NO: 5)

An expression plasmid pDAO-23, carrying the cDNA for R. toruloides DAO, was constructed using a pET23a vector and introduced into E. coli BL21 [DE3]. Isopropyl-1-thio-β-D-galactoside (IPTG)-induced transformants exhibited DAO activity in cell lysates, indicating that active DAO was expressed in *E. coli*. SDS/PAGE analyses of the cell lysates revealed a distinct 37 kDa protein band, the estimated size of the DAO subunit, which was not present in the lysate similarly prepared from the pET23a transformed host. The protein was fully induced within 30 min. of IPTG induction. DAO was purified to near homogeneity using Ni-column chromatography. Approximately 4 mg of the protein could be obtained in one step from 250 ml of *E. coli* culture. The purified protein showed a specific activity of 1,211 U/mg, a 7-fold increase over that of crude extract and a 20-fold increase over that of the purified *R. toruloides* DAO protein. The activity is similar to that of the enzyme prepared by dialysis in the presence of FAD, indicating that the recombinant DAO may contain FAD as a prosthetic group.

A DAO-expressing *E. coli* strain, pDAO23-transformed DH5α, was also prepared and has been deposited with the American Type Culture Collection as No. 98485.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of this invention.

For example, the DAO proteins of the invention include, but are not limited to, recombinant proteins, natural proteins, and synthetic proteins as well as proteins which are preproteins or proproteins. Recombinant DAO proteins include a DAO with contiguous or non-contiguous amino acid deletions or a DAO containing a signal peptide which allows for transport into the various compartments of a cell, such as the periplasmic space, endoplasmic reticulum, mitochondria, or the extracellular space.

What is claimed is:

1. An isolated nucleic acid comprising SEQ ID NO: 1 or SEQ ID NO: 2.

2. A vector containing the nucleic acid of claim 1.

3. A transformed host cell containing the nucleic acid of claim 1.

4. An isolated nucleic acid consisting of SEQ ID NO: 1 or SEQ ID NO: 2.

5. A vector containing the nucleic acid of claim 4.

6. A transformed host cell containing the nucleic acid of claim 4.

* * * * *